United States Patent [19]
Gordon

[11] 4,250,880
[45] Feb. 17, 1981

[54] STABILIZING FITTING FOR AN INTRAVENOUS CATHETER

[75] Inventor: Marvin Gordon, East Windsor, N.J.

[73] Assignee: Whitman Medical Corporation, Clark, N.J.

[21] Appl. No.: 46,803

[22] Filed: Jun. 8, 1979

Related U.S. Application Data

[63] Continuation-in-part of Ser. No. 5,032, Jan. 19, 1979, which is a continuation-in-part of Ser. No. 905,399, May 12, 1978, abandoned.

[51] Int. Cl.³ ............................................. A61M 5/00
[52] U.S. Cl. ................................ 128/214 R; 128/348; 128/DIG. 26
[58] Field of Search ............... 128/133, 214 R, 214.2, 128/214.4, 221, 215, 347–350, DIG. 26

[56] References Cited
U.S. PATENT DOCUMENTS

| 2,525,398 | 10/1950 | Collins | 128/215 |
| 2,707,953 | 5/1955 | Ryan | 128/214 R |
| 3,059,645 | 10/1962 | Hasbrouck et al. | 128/DIG. 26 |
| 3,167,072 | 1/1965 | Stone et al. | 128/133 |
| 3,856,020 | 12/1974 | Kovac | 128/347 |
| 4,020,835 | 5/1977 | Nordstrom et al. | 128/214.4 |
| 4,082,094 | 4/1978 | Dailey | 128/214 R |
| 4,129,128 | 12/1978 | McFarlane | 128/133 |
| 4,161,177 | 7/1979 | Fuchs | 128/214.4 |

Primary Examiner—Dalton L. Truluck
Attorney, Agent, or Firm—Holman & Stern

[57] ABSTRACT

A stabilizing fitting for securely holding an intravenous catheter to a patient's skin at a venipuncture site comprises a laminar base member with an adhesive lower surface and a catheter hub retaining cradle on its upper surface. After insertion of the catheter into a vein and connection to an infusion tube, the catheter hub is pressed into the cradle which locates the hub laterally and longitudinally and the fitting is dabbed onto the patient's skin. Stabilization is then achieved by affixing criss-cross adhesive tapes over the assembly.

10 Claims, 20 Drawing Figures

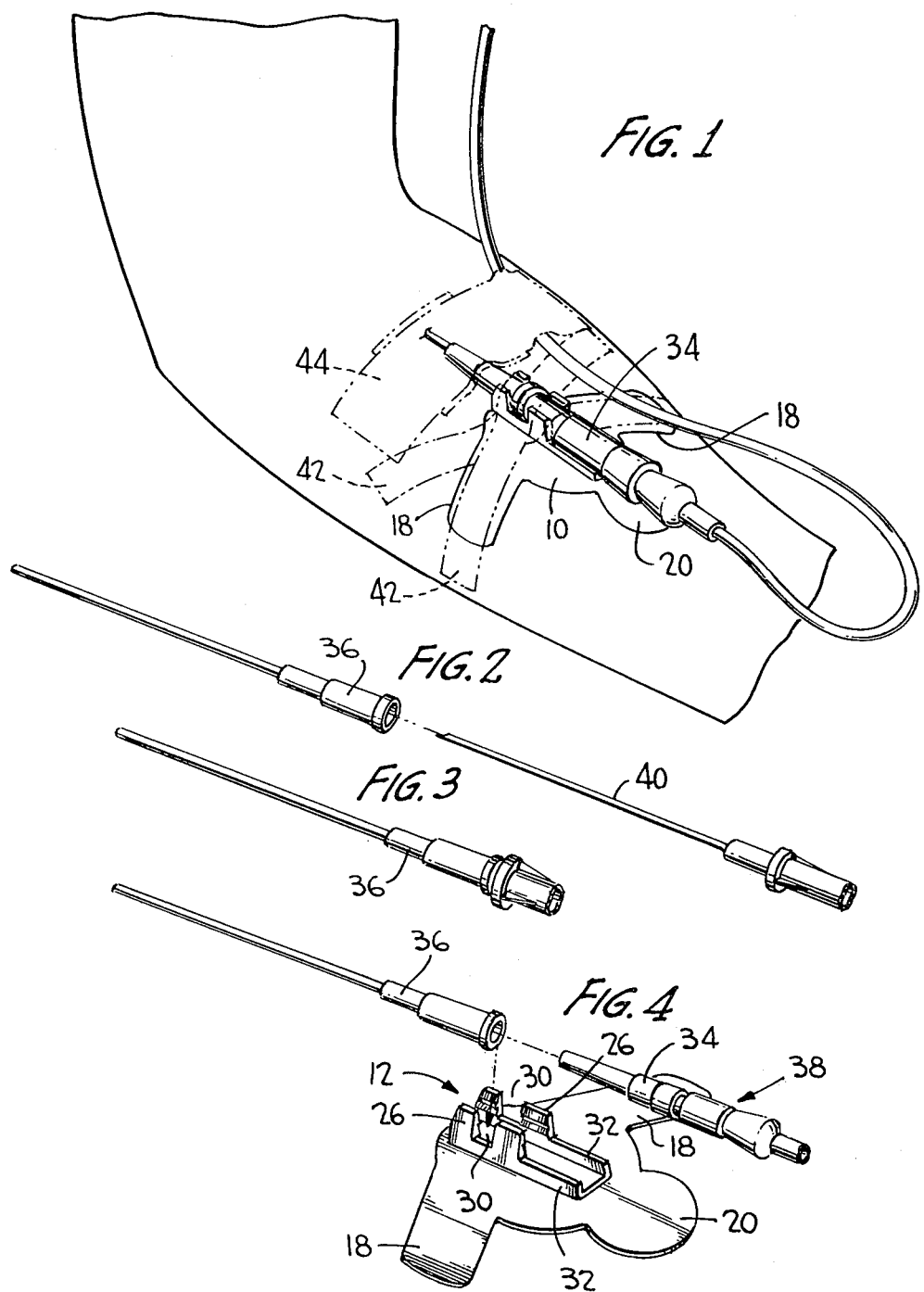

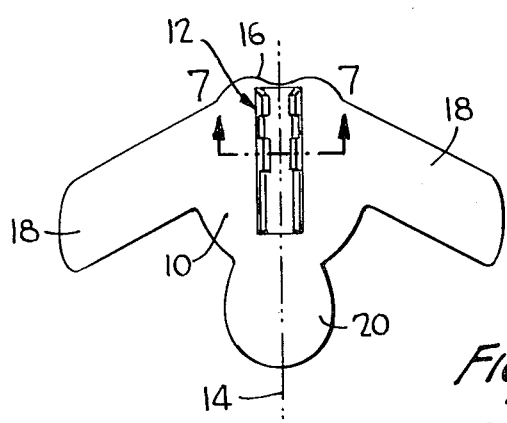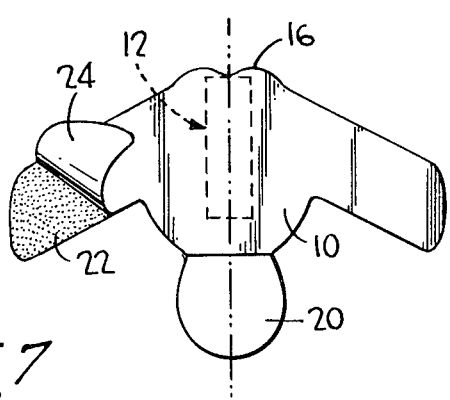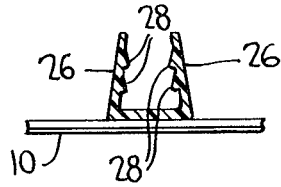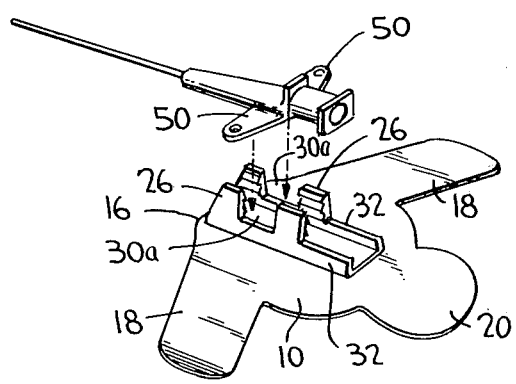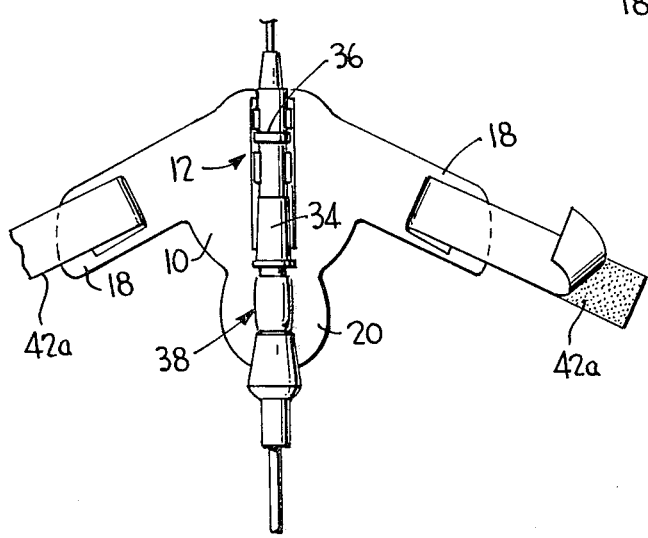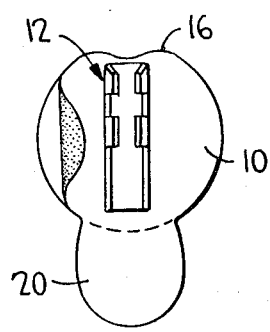

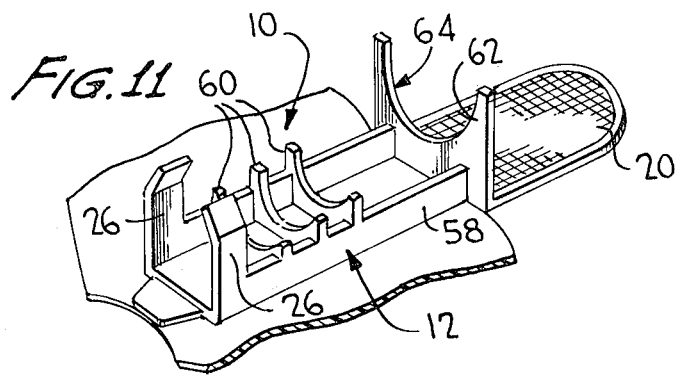
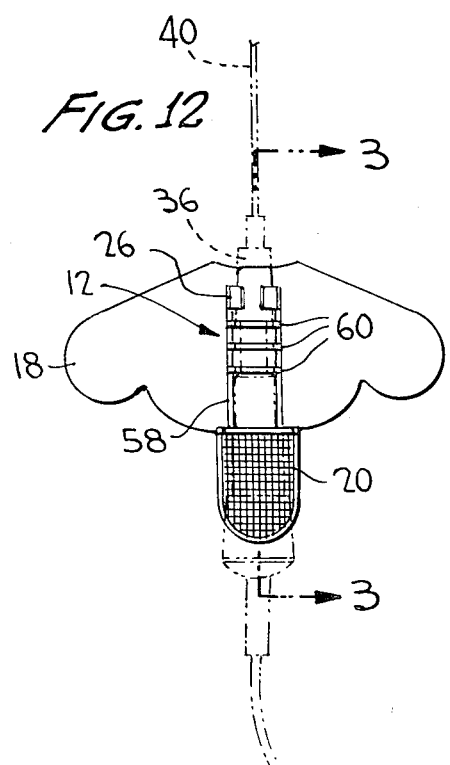
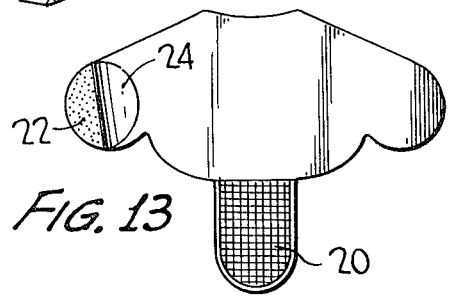
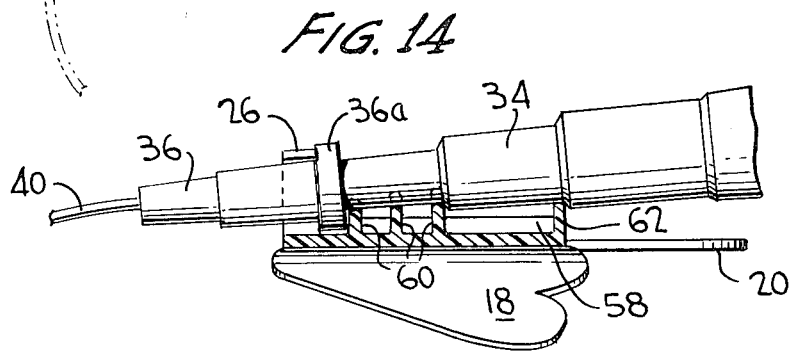
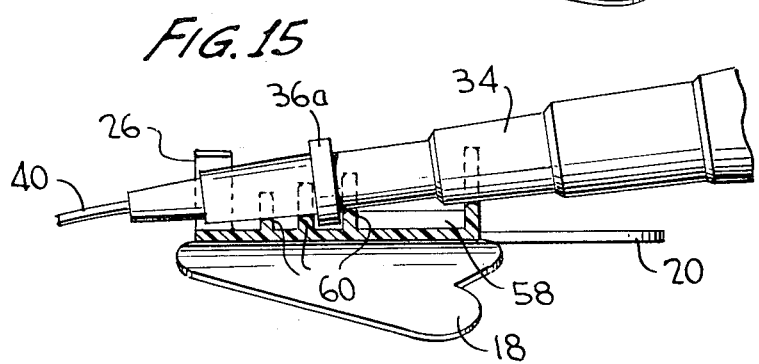

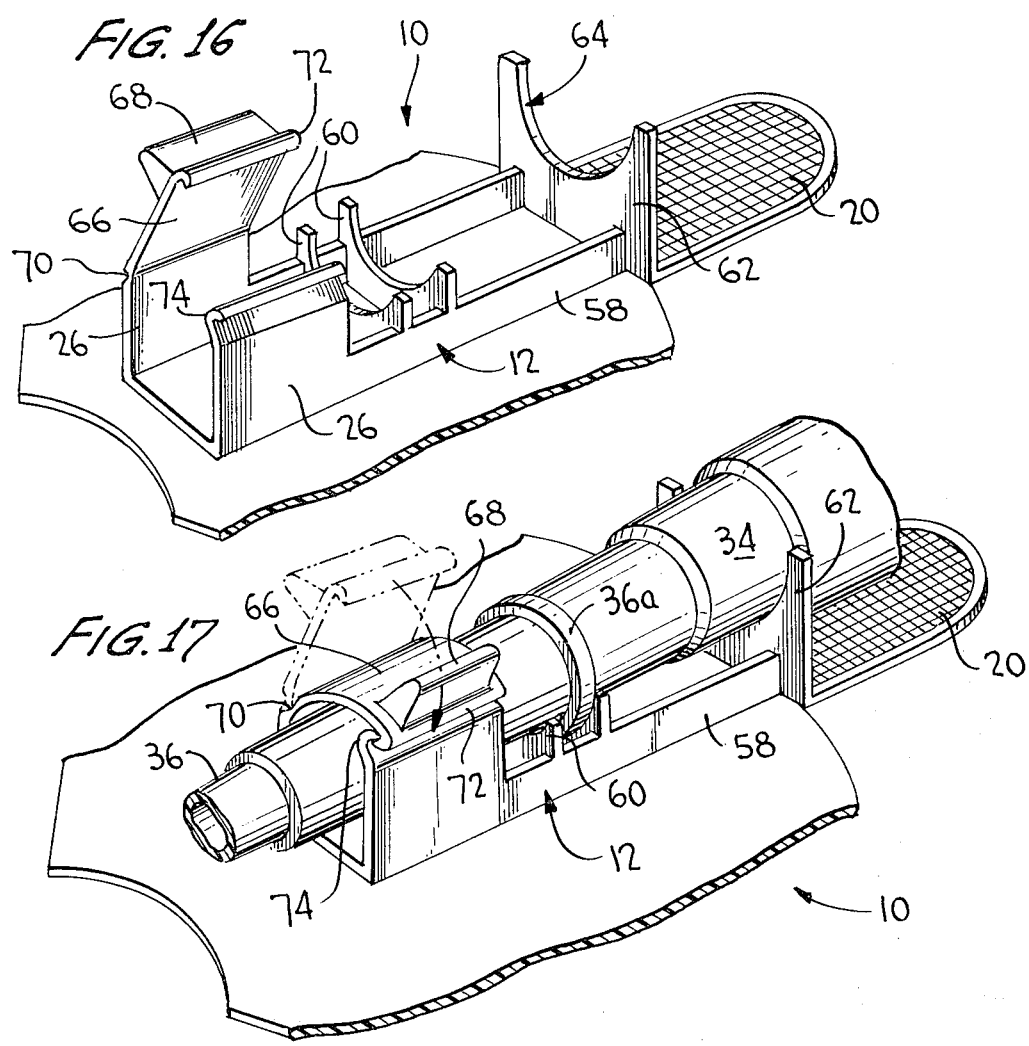

STABILIZING FITTING FOR AN INTRAVENOUS CATHETER

BACKGROUND OF THE INVENTION

This application is a continuation-in-part of copending application Ser. No. 5,032, filed Jan. 19, 1979, which is in turn a continuation-in-part of copending application Ser. No. 905,399, filed May 12, 1978, now abandoned.

The invention relates to fittings for use in intravenous infusion procedures for securing an intravenous catheter in a stabilized manner to a patient's skin.

A venipuncture can be made in many areas of the body, such as the forearm, back of the hand, upper arm, ankle or foot. In this procedure, a catheter is normally inserted into a vein by means of a hollow needle which is then withdrawn to avoid damage to the walls of the punctured vein. The catheter remains attached to the patient and is connected to a source of infusion liquid. It is then necessary to stabilize the catheter to prevent movement tending to work the catheter loose and leading to potential source of infection or irritation to the patient at the point of catheter insertion. This stabilization is generally done by taping the catheter hub and associated tube fittings to the patient's skin in an area adjacent to the point of catheter insertion.

It is important to obtain secure stabilization of the inserted catheter and if the stabilizing procedure relies on the individual taping technique of a person performing the venipuncture, this is a possible source of insecurity of stabilization.

OBJECTS OF THE INVENTION

It is an object of the invention to provide a fitting which can be used to provide a standardized technique for securely stabilizing an intravenous catheter to a patient in an intravenous infusion procedure.

It is a further object of the invention to provide a fitting for securely holding the hub of an intravenous catheter and its associated tubing so as to allow efficient stabilization of the catheter at any selected infusion site.

Another object of the invention is to provide a catheter securing and stabilizing fitting which allows the catheter to be held securely in place while still facilitating access to the point of the catheter insertion into the skin and visual access to the point of blood flashback in the infusion tubing.

A further object of the invention is to provide a fitting for cradling and securely holding a catheter in place on a patient's skin with the catheter hub being held out of contact with the skin and at a suitable angle to avoid crimping or bending of the catheter itself.

BRIEF SUMMARY OF THE INVENTION

A disposable catheter stabilizng fitting of synthetic plastics material is provided which comprises a catheter hub-retaining cradle on a laminar base member having an adhesive undersurface and a tab grip extending rearwardly of the cradle.

In use, when the catheter has been inserted into a patient's vein and the catheter hub has been connected to an infusion tube, the hub is pressed with a snap-fit into the cradle and the fitting with attached hub and tubing is dabbed onto the patient's skin (after removal of a protective covering for the adhesive on the fitting's undersurface). Then, the fitting can be securely stabilized in position by overlaying it with criss-cross adhesive taper.

The cradle is designed to hold the catheter hub at a suitable angle to avoid bending or crimping of the catheter and with the catheter itself projecting forwardly from the front end of the fitting. This facilitates access to the point of catheter insertion into the skin so that a gauze pad of the like can be attached over this point and removed if required for inspection purposes without disturbing the secure attachment of the fitting. Further, the cradle and base member are designed to provide visual access to the point of blood flashback rearwardly of the catheter hub even when the fitting is secured by the criss-cross tapes.

In one preferred form of the invention, the base member is provided with laterally extending rearwardly inclined elongated wings positioned to serve as guides over which the criss-cross tapes are laid and the fitting may be supplied with such tapes having their ends preattached to these wings.

BRIEF DESCRIPTION OF THE DRAWINGS

FIG. 1 is a perspective view of an intravenous infusion site in a patient's forearm showing the use of a stabilizing fitting in accordance with the invention:

FIGS. 2 and 3 are perspective views of a conventional form of over the needle catheter set in retracted and assembled conditions respectively;

FIG. 4 is a perspective view of one form of stabilizing fitting in accordance with the invention showing a catheter hub and associated infusion tube fitting about to be attached thereto;

FIG. 5 is a plan view of the fitting shown in FIG. 4;

FIG. 6 is an underneath view of the same fitting;

FIG. 7 is a section on line 7—7 of FIG. 5;

FIG. 8 is a plan view of an infusion site showing the use of a modified form of fitting in accordance with the invention;

FIG. 9 is a perspective view of an alternative type of stabilizing fitting and catheter;

FIG. 10 is a plan view of another form of stabilizing fitting;

FIG. 11 is a perspective view of part of a still further form of stabilizing fitting;

FIG. 12 is a plan view of the fitting shown in FIG. 11 with a catheter hub and associated infusion tubing in place;

FIG. 13 is an underneath view of the fitting shown in FIGS. 11 and 12;

FIG. 14 is a section on line B—B of FIG. 12;

FIG. 15 is a similar view to that shown in FIG. 14 but with the catheter hub shown in a different position on the fitting;

FIG. 16 is a perspective view of part of another form of stabilizing fitting;

FIG. 17 is a view similar to FIG. 16 showing a catheter hub in place;

DESCRIPTION OF THE PREFERRED EMBODIMENTS

Figure 18:
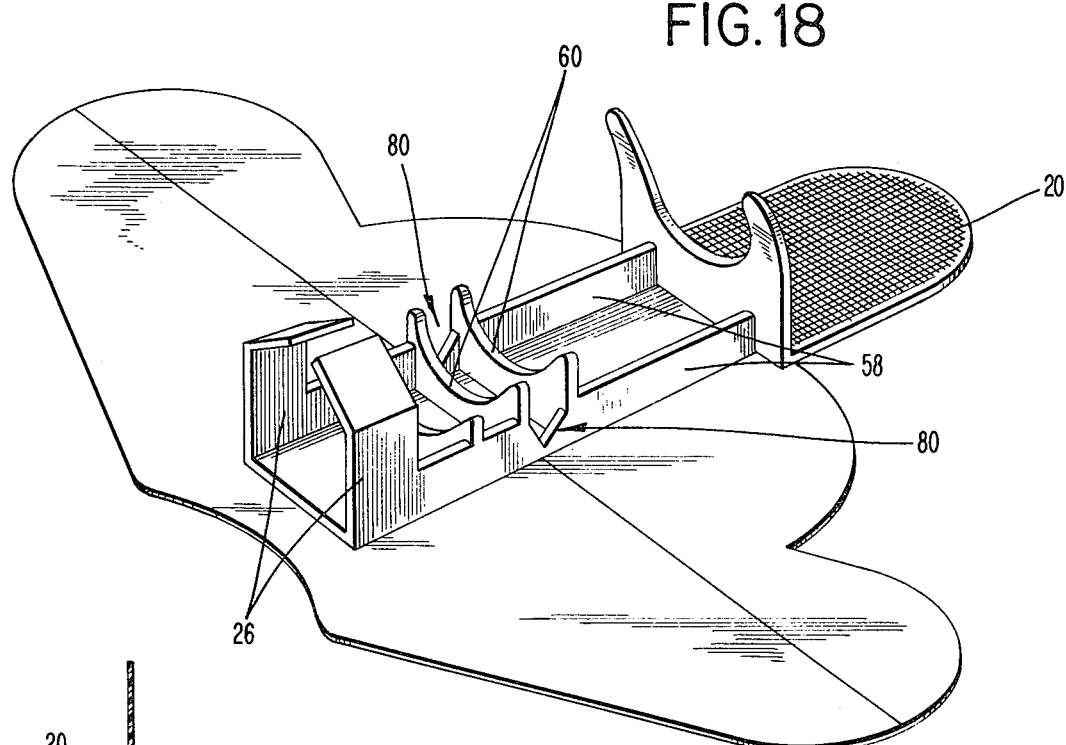
FIG. 18 is a perspective view of yet another form of stabilizing fitting.

As best illustrated in FIGS. 4–7, a first preferred form of catheter stabilizing fitting comprises a laminar base member 10 of synthetic plastics material such as PVC, polyethylene or the like and a catheter hyb-retaining cradle 12 of like or similar material on the upper surface of the base member. The cradle and base member may be separately formed as by molding or stamping and adhesively assembled together or alternatively the entire fitting may be integrally formed as a single molded item.

The base member is symmetrical about a longitudinal axis 14, has a forward end 16 and laterally extending rearwardly inclined elongated wings 18 with an included angle therebetween of about 120°. A tab grip 20 is provided as a rearward extension of the base member and the entire undersurface of the base member, except for the tab grip, is provided with a coating of any suitable pressure-sensitive adhesive 22 (FIG. 6) and a protective strippable covering sheet 24.

The cradle 12 has side walls 26 of resilient plastics, which converge upwardly towards their free upper edges, and which are provided internally with longitudinal ridges 28. Each side wall has a central opening 30 and rearwardly of the side walls the cradle is extended into a section including elongated reduced height extensions 32 of the side walls. The cradle is dimensioned to accept a standard catheter hub 36 and associated infusion tube fittings 38 as shown in FIGS. 1 and 4 by press fitting the hub into the cradle between the side walls. In this condition, the resiliency of the side walls and their internal ribs firmly locate the hub in position and positive longitudinal location of the hub is obtained by the hub boss fitting in the wall openings 30.

The stabilizing fitting is conveniently supplied in a kit including for example an over the needle catheter, antiseptic liquid and applicator, adhesive tapes, and gauze padding. A preferred method of using the fitting in an intravenous infusion procedure is illustrated in FIGS. 1-4. A venipuncture is made in the normal way and the needle 40 is withdrawn from the catheter. After checking the blood flashback, the catheter hub 36 is connected to its associated infusion tube fittings 38 and then the stabilizing fitting 10, held by means of tab 20, is brought from below the hub and the hub is snapped into the cradle 12. The protective covering sheet 24 having been stripped from the undersurface of the fitting, the fitting is dabbed onto the patient's skin to temporarily stabilize the catheter and after forming a conventional bight in the infusion tubing as shown in FIG. 1, the fitting is taped down with criss-cross adhesive tapes 42 passing over the wings 18 which serve as alignment guides for the tapes.

A conventional gauze pad and covering tape 44 is placed over the point of insertion of the catheter into the patient's skin. As shown in FIGS. 1 and 4 in the assembled condition of the equipment, the enlarged diameter portion 34 of the forward fitting of the infusion tubing sits on the reduced height side wall extensions 32. This establishes a suitable angle for the catheter after taping down, to prevent crimping or kinking of the catheter.

It will be seen that by using the stabilizing fitting in the described manner, a simple means is provided for securely stabilizing the catheter according to a standardized procedure in a rapid and effective manner. Moreover, with the catheter projecting from the front end of the stabilizing fitting ready access is available to the point of catheter insertion, for inspection purposes, by removing the gauze pad without disturbing the stabilization of the catheter. Further, the point of blood flashback in the tubing behind the catheter hub is at all times visible due to the positioning of the criss-cross tapes over the wings 18 which are designed to cross the tapes over the hub boss as shown (to this end the center lines of the respective wings pass substantially through the centers of the openings 30).

FIGS. 8-10 show modified forms of fittings in accordance with the invention. The fittings shown in FIG. 8 are substantially similar to that previously described except that it is supplied with adhesive tapes 42a provided with suitable release paper and having the ends preattached to the upper surfaces of the wings 18. FIG. 9 shows a fitting in which the openings 30a in the side walls are wider than in the previous embodiments to receive and longitudinally locate a catheter hub having lateral wings 50. FIG. 10 shows a fitting in which the wings 12 are omitted. It will be appreciated that the fittings shown in FIGS. 8-10 are in their essential features equivalent to the fittings shown in the previous figures and their manner of use is essentially similar.

FIGS. 11-15 show a further form of fitting having a modified type of cradle. In other respects and in its manner of use, this fitting is similar to those shown in FIGS. 1-9 and like references are used to denote these similar parts. The cradle 12 in this case has side walls 26 and a trough-like cradle section 58 rearwardly of walls 26 formed with three longitudinally spaced part-circular abutment ribs 60. At its rear, the cradle terminates in a lateral wall 62 having a part-circular opening 64.

The fitting is used in the same way as those previously described and in use, as shown in FIGS. 12, 14 and 15, when the forward end of a catheter hub 36 is pressed into place between the side walls, the boss 36a of the hub will be longitudinally located by resting between the rear end of the walls 26 and the forwardmost rib 60 or by resting between a pair of the ribs 60 and with the forward end of the infusion fitting 34 resting in the opening 64 in rear wall 62 of the cradle. Longitudinal and transverse location of the catheter hub is therefore provided by the walls 26, the ribs 60 and the opening 64, and the heighth of the rear wall 62 beneath the opening 64 establishes the correct catheter angle to prevent kinking or crimping. The construction is such that the catheter boss 36a can be located between walls 26 and the forwardmost rib 60 or between adjacent pairs of ribs to longitudinally maintain the hub in position.

As indicated, the fitting shown in FIGS. 11-15 is used in like manner to those previously described and can likewise be provided with cross-cross tapes 42 on its wing portions 18.

The fitting shown in FIGS. 16 and 17 is similar to that shown in FIGS. 11-15 and like references are again used to denote like parts. In this case, the side walls 26 are extended somewhat rearwardly compared with the embodiment of FIGS. 11-15 and the forwardmost rib 60 is eliminated. One of the walls 26 carries a snap-over strap or cover 66 with a thumb grip 68, the cover 66 being integrally molded with the wall 26 about a hinge line 70 of reduced cross section. Cover 66 terminates in a latch member 72 which engages a complementary latch member 74 at the top of the opposite wall 26.

Use of this fitting is similar to the previously described embodiment. The catheter hub is pressed into place between walls 26, with the cover 66 open. The boss 36a of the catheter hub is axially located as shown and the cover 66 is then brought across and latched into place. The material of the walls 26 and of the cover should provide sufficient flexibility to enable the cover to conform to the outer surface of the catheter hub and to accommodate the slight misalignment between the axis of the catheter hub and the line of the hinge 70.

The snap-over cover allows this form of fitting to dispense with the use of criss-cross tapes, and when required, the latch members 72 and 74 can be released and the cover opened by inward pressure on walls 26.

Figure 20:
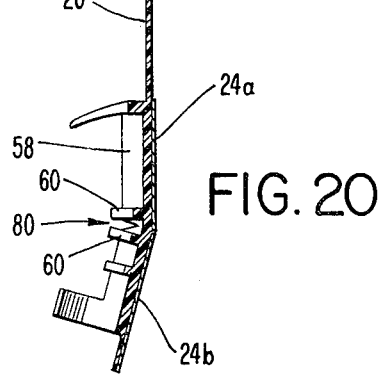
FIG. 20 is a longitudinal section through the fitting shown in FIG. 18 in a bent condition.
Figure 19:
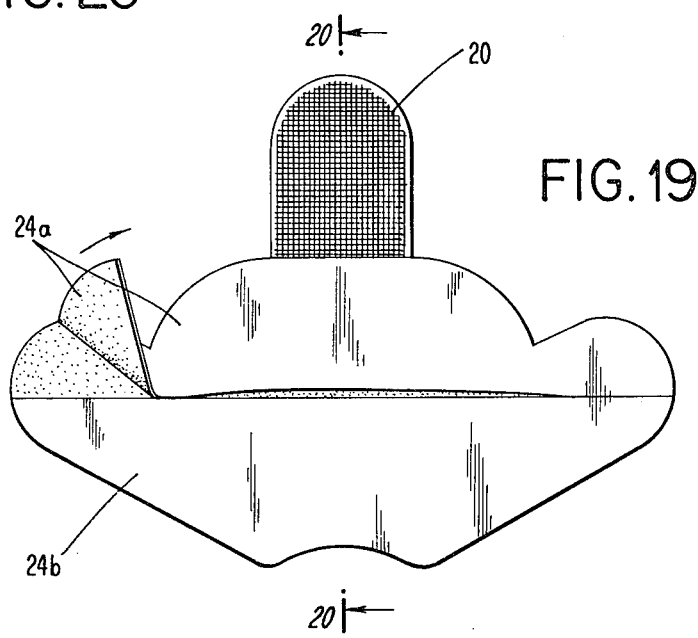
FIG. 19 is an underneath plan of the fitting shown in FIG. 18.

FIGS. 18-20 show a fitting which is again similar to that shown in FIGS. 11-15. This time however, the fitting is provided with means for reducing the bending resistance of the fitting along a line substantially transverse to the longitudinal axis of the fitting. Such means take the form of substantially V-shaped notches 80 in the walls of the cradle-like trough section 58 between a pair of the ribs 60. These notches facilitate bending or folding of the fitting as shown in FIG. 20 which assists in manipulating the fitting when this is being applied to a patient's skin. Further, the release paper on the underneath surface of the fitting is in this case provided in two halves 24a and 24b which meet on the bending axis so that when the fitting is bent as shown, this also facilitates removal of the release paper. Any of the other fittings herein disclosed can also be provided with similar bending resistance reducing means and split release paper.

While several examplary embodiments of the invention have been described in detail, the invention is not limited to the specific features thereof and modifications can be made within the scope of the invention as defined in the appended claims.

The embodiments of the invention in which an exclusive property or privilege is claimed are defined as follows:

1. A stabilizing fitting for securing an intravenous catheter to a patient's skin comprising a laminar base member having a longitudinal axis, an upper surface and a lower surface, pressure-sensitive adhesive means on at least a part of said lower surface of said base member, a catheter hub-retaining cradle on said upper surface of said base member, said cradle having a forward end, a rearward end and resilient side walls substantially parallel to and symmetrically disposed on opposite sides of said longitudinal axis, said side walls being formed to receive and laterally locate a catheter hub pressed into said cradle, locating means associated with said cradle for maintaining said hub in position longitudinally of said axis with the catheter projecting substantially axially from said forward end of said cradle, a tab grip froming an extension of said base member rearwardly of said cradle, and means for reducing the bending resistance of the fitting along a bending axis substantially perpendicular to said longitudinal axis and located intermediate the forward and rearward ends of said cradle.

2. The fitting of claim 1 wherein said bending resistance reducing means comprises notch means formed in opposite side wall portions of said cradle.

3. The fitting of claim 1 wherein said cradle includes a trough-like portion rearwardly of said side walls and said bending resistance reducing means comprises notch means formed in opposed side wall portions of said trough-like portion.

4. The fitting of claim 3 wherein said trough-like portions includes a pair of laterally extending catheter hub-retaining ribs and said notch means is located between said ribs.

5. The fitting of claim 1 including a pair of release papers covering said pressure sensitive adhesive means, said release papers meeting on a line corresponding with said bending axis.

6. The fitting according to claim 1 wherein said tab grip is substantially co-planar with said base member and is free of said adhesive means.

7. The fitting according to claim 1 wherein said cradle includes a trough-like portion rearwardly of said side walls and said locating means includes laterally extending rib means in said trough-like portion for longitudinally locating a catheter of boss portion.

8. The fitting according to claim 7 wherein said trough-like portion includes a laterally extending rear wall having an opening for receiving and laterally locating an infusion fitting associated with a catheter hub.

9. The fitting according to claim 1 wherein said cradle includes a bottom and a top, and wherein said rearward end is defined by a rear support wall having a top edge which is recessed to a height above said bottom of said cradle to receive and support a hub of the catheter at a hub location such that the catheter hub is supported at a small angle relative to said upper surface of said laminar base member.

10. The fitting according to claim 9 wherein said locating means comprises a plurality of further support walls arranged parallel to said rear support wall, said further support walls being recessed to progressively higher levels above said bottom of said cradle with the forwardmost further support wall being recessed to the lowest such level.

* * * * *